United States Patent [19]

Klein

[11] Patent Number: 5,208,013
[45] Date of Patent: May 4, 1993

[54] COMPOSITION FOR SKIN CARE AND PROTECTION

[75] Inventor: Kenneth Klein, Fairlawn, N.J.

[73] Assignee: Olympus International, Inc., Salt Lake City, Utah

[21] Appl. No.: 709,694

[22] Filed: Jun. 3, 1991

[51] Int. Cl.$^5$ .......................... A61K 7/40; A61K 7/42; A61K 7/44; A61K 7/48
[52] U.S. Cl. ........................................ 424/59; 424/47; 424/60; 514/772; 514/847; 514/937; 514/938
[58] Field of Search ....................... 424/59, 60; 514/847

[56] References Cited

U.S. PATENT DOCUMENTS 4,894,222 1/1990 Matravers ........................... 514/865

OTHER PUBLICATIONS

Harry, Cosmetic Materials, 1963, vol. 2, pp. 21 and 22.
Cosmetics and Toiletries, Nov. 1986, vol. 101, pp. 125, 126, 128, 130, 132, 134, 136 and 138.

Primary Examiner—Dale R. Ore
Attorney, Agent, or Firm—K. S. Cornaby

[57] ABSTRACT

A composition for topical application to the skin of a human being is disclosed which provides a barrier against irritation and painful damage due to contact with many otherwise harmful materials. The composition comprises in combination water, dimethicone, stearic acid, coconut fatty acid, isopropyl myristate, glycerin, triethanolamine, cetyl alcohol, polyvinyl pyrrolidone, cetearyl alcohol, ceteareth-20, tetrasodium EDTA, hydroxyethyl cellulose, aloe vera gel, vitamin E and lanolin.

5 Claims, No Drawings

COMPOSITION FOR SKIN CARE AND PROTECTION

BACKGROUND OF THE INVENTION

1. Field of the Invention

The present invention relates to compositions or preparations that are applied to the skin of a human being to provide a protective barrier against numerous irritants, chemicals and other materials which are harmful to the skin.

2. State of the Art

Soaps, detergents and other cleaning agents have long been used in cleaning the skin of a human being. Unfortunately, even many of the cleaning compositions including water itself when used repeatedly can become irritants which cause acute irritation, damage and pain to the skin. Further, there are numerous other materials which one comes into contact with on a daily basis that can cause irritation and damage to the skin. Caustics used in many different compositions can be harmful to one's skin. Paints, pastes, glues, solvents, drying agents, acids, fiberglass and chemicals used therewith, lime, cement, grease, disinfectants and other chemicals which can be very harmful to the skin are commonly encountered in the home as well as in one's occupational pursuits.

Lotions and cremes have been used to moisturize and sooth irritated skin. Skin barriers comprising a physical covering placed over the skin, including rubber gloves and liquid products that leave a layer of impermeable material on the skin, are known. However, such physical barriers themselves can become harmful by interfering with the normal operation of the skin, such as perspiration. In addition, the physical barriers can allow irritants to infiltrate between the barrier and the skin, whereupon the barriers give no protection whatsoever and actually become a liability.

There has been a long felt need for a creme or paste which could be applied to one's skin to be absorbed in and on the surface of the skin to provide an effective, invisible barrier against most materials that can cause irritation and damage to the skin. There have been compositions such as those disclosed in U.S. Pat. No. 4,950,688 that are said to restore or enhance the natural skin barrier function when the skin surface has become excessively dry, fissured, eroded or otherwise damaged, but there is a lacking of any effective composition to augment and provide an improved skin barrier function to skin that has not already lost its natural barrier function. There has been a long felt need for a composition that could be applied to one's skin to be absorbed in and on the surface of the skin and that would provide an invisible, nondiscernable barrier far superior to the natural barrier function of the skin. Unfortunately, heretofore there has been no such effective product available.

3. Objectives

A principal objective of the invention is to provide a novel composition for application to the skin of a human being to augment the natural skin barrier function of the skin and provide an invisible, nondiscernable barrier that is far superior to the natural barrier function of the skin.

A particular objective of the present invention is to provide such a composition for application to one's skin wherein the composition forms a superior barrier to harmful substances and chemicals that would otherwise cause irritation and painful damage to the skin.

An additional objective of the present invention is to provide such a composition for application to one's skin wherein the composition forms an effective barrier layer on the surface of the skin but is invisible and nonperceptible so that the user can go about normal activities without otherwise even knowing that the composition is present.

A still further objective of the present invention is to provide such a composition for application to one's skin that provides effective barrier protection for the skin for up to 4 hours or more even after washing and scrubbing of the skin with water and skin cleansers.

DESCRIPTION OF THE INVENTION

The above objectives are achieved in accordance with the present invention by providing an improved composition for topical application to the skin of human beings. The composition may be formulated as a creme, lotion, liquid or aerosol. By utilizing a particular, new and novel combination of ingredients, an improved composition is provided that forms a particularly effective skin barrier that will protect one's skin for up to 4 hours even when the skin is subjected to repeated washing with water and skin cleansers during the 4 hour period.

The skin protectant composition of the present invention provides an exceptionally effective barrier that protects the skin to which the composition has been applied from a great many materials that are harmful to the skin. The composition of the present invention provides exceptional protection from such harmful materials as harsh soap, detergents, alcohol, oil, dirty grease, organic solvent, dyes, polishing compounds, acids, alkalies, bleach, chlorine, salt water, paints and most chemical one might encounter including industrial chemicals.

The composition of the present invention comprises the following ingredients (with preferred concentrations given in percent by weight): deionized water (80 to 90%), dimethicone (2 to 6%), stearic acid (1 to 3%), coconut fatty acid (1 to 3%), isopropyl myristate (1 to 3%), glycerin (1 to 3%), triethanolamine (1 to 3%), cetyl alcohol (1 to 3%), polyvinyl pyrrolidone (1 to 3%), cetearyl alcohol (1 to 3%), ceteareth-20 (1 to 3%), tetrasodium EDTA (0.1 to 0.9%), hydroxyethyl cellulose (0.1 to 0.9%), aloe vera gel (0.1 to 0.9%), vitamin E (0.1 to 0.9%) and lanolin (0.1 to 0.9%). In addition, the composition can include stabilizers and preservatives such as methylparaben (0.1 to 0.9%) and propylparaben (0.05 to 0.5%). The cetearyl alcohol and ceteareth-20 are advantageously incorporated into the composition by adding a commercially available product known as Promulgen D which is manufactured and marketed by Amerchol Company of Amerchol Park, Edison, N.J. 08817.

The composition of the present invention has been proven effective in many clinical tests and by tests in which the composition is used in actual use. In tests made by medical personnel, including doctors and dentists, the composition of the present invention provides a barrier shield from the many chemicals that such professional people come in contact with during their normal activities. Doctors and dentist have particularly found that the composition is effective to prevent irritation due to repeated washing of their hands with strong, biocidal cleansers. In addition, the composition prevents irritation and chafing due to rubber gloves that are repeatedly put on and then removed.

The composition is highly advantageous for the home consumer. It has been found to provide protection against paints, pastes, glue, drying agents, cleaning agents and spray products that the average person comes in contact with on a daily basis. The housewife hands can be protected from repeated washings with harsh soaps and from contact with caustic cleaners such as oven cleaning compositions. The composition further protects one's skin when doing outdoor work, such as gardening. Superior protection is achieved from irritation due to various plants, dirt, chemicals, sprays and allergies.

The composition is useful in working around the home and garage. The composition provides protection from contact with grease, dirt, water, saline solutions, solvents, cleaners, waxes, polishes. The product has been found to have a unique property in that contact with aromatic materials will not leave a lingering smell on the skin. Housewives find that onions and garlic smells can be washed away with soap and water. Those who happen to occasionally have gasoline and other petroleum products come in contact with their skin can wash the smelly materials from their skin using plain soap and water, with no lingering smell on the skin.

Industrial and trade workers have found that the composition provides superior protection and shields their hand and skin from most acids, caustics, plating solutions, fiberglass and organic chemicals used in fabricating fiberglass items, lime, cement, grease and dirt. Masons and others working with lime and cement have found the composition to completely protect their hands and skin without the painful irritation that has heretofore simply been accepted as a vocational handicap.

In actual clinical tests, the composition as given above was applied to a persons hands. The composition was rubbed into the person's skin and allowed to dry for 5 minutes. In one test, strong, concentrated acids including sulfuric and hydrochloric acids was placed on the palm of the person's hand and allowed to remain in the palm of the hand for up to one to two minutes. No burning, irritation or pain was experienced by the person. The test was repeated using strong caustic agents such as lye found in oven cleaners. Again, the caustic agents remained in contact with the palm of the person's hand for several minutes without burning, irritating or causing any damage to the skin. The person felt no burning or pain of any kind. After repeated washing of the person's hands with cleansers of various kinds, the tests were repeated and the same results obtained.

Although a preferred embodiment of the skin protecting composition of the present invention has been illustrated and described, it is to be understood that the present disclosure is made by way of example and that various other embodiments are possible. For example, in certain applications such as for use by doctors, dentists and other health professionals, it is advantageous to add a bactericide to the composition. Representative bactericides that can be added to the composition include benzalkonium chloride, tricolosan, benzethonium Chloride and phenol. In another example, when the composition is being used by persons who are exposed to the sun, a sun screen or ultraviolet light screening agent can be added to the composition. Representative sun screen and ultraviolet light screening agents include benzophenone-3, padimate-O, ethylhexyl p-methoxycinnamate, titanium dioxide and octyl salicylate.

Other various embodiments are possible without departing from the subject matter coming within the scope of the following claims, which subject matter is regarded as the invention.

I claim:

1. A composition for topical application to the skin of a human being which provides a barrier against irritation and painful damage due to contact with many otherwise harmful materials, said composition comprising in combination water, dimethicone, stearic acid, coconut fatty acid, isopropyl myristate, glycerin, triethanolamine, cetyl alcohol, polyvinyl pyrrolidone, cetearyl alcohol, ceteareth-20, tetrasodium EDTA, hydroxyethyl cellulose, aloe vera gel, vitamin E and lanolin.

2. A composition in accordance with claim 1 wherein the water is deionized water.

3. A composition in accordance with claim 1 wherein water is present in an amount of 80 to 90 percent by weight; dimethicone is present in an amount of 2 to 6 percent by weight; stearic acid, coconut fatty acid, isopropyl myristate, glycerine, triethanolamine, cetyl alcohol, polyvinyl pyrrolidone, cetearyl alcohol and ceteareth-20 are each present in an amount of 1 to 3 percent by weight; and hydroxyethyl cellulose, tetrasodium EDTA, aloe vera gel, vitamin E and lanolin are each present in an amount of 0.1 to 0.9 percent by weight.

4. A composition in accordance with claim 1 further including a bacteriocidal agent.

5. A composition in accordance with claim 1 further including a sun screen agent.

* * * * *